United States Patent [19]
Bemis et al.

[11] Patent Number: 5,945,407
[45] Date of Patent: Aug. 31, 1999

[54] METHODS AND COMPOSITIONS USING BUTYRATE ESTERS OF THREITOL

[75] Inventors: Guy W. Bemis, Arlington; Pravin R. Chaturvedi, Quincy, both of Mass.

[73] Assignee: Vertex Pharmaceuticals, Incorporated, Cambridge, Mass.

[21] Appl. No.: 09/015,811

[22] Filed: Jan. 29, 1998

Related U.S. Application Data

[62] Division of application No. 08/550,453, Oct. 30, 1995, Pat. No. 5,763,488.
[51] Int. Cl.$^6$ .................. A61K 31/70; A61K 31/225; A61K 31/17
[52] U.S. Cl. ..................... 514/43; 514/547; 514/588
[58] Field of Search ............................ 514/547, 43, 588

[56] References Cited

U.S. PATENT DOCUMENTS

| | | | |
|---|---|---|---|
| 5,569,675 | 10/1996 | Rephaeli | 514/547 |
| 5,763,488 | 6/1998 | Bemis et al. | 514/547 |

OTHER PUBLICATIONS

Charles Chany and Italina Cerutti, "Antitumor Effect of Arginine Butyrate in Conjunction with *Corynebacterium Parvum* and Interferon," *Int. J. Cancer*, vol. 30, pp. 489–493 (1982).
Zi–Xing Chen and Theodore R. Breitman, "Tributyrin: A Prodrug of Butyric Acid for Potential Clinical Application in Differentiation Therapy," *Cancer Research*, vol. 54, pp. 3494–3499 (1994).
Anne F. Collins et al., "Oral Sodium Phenylbutyrate Therapy in Homozygous β–Thalassemia: A Clinical Trial," *Blood*, vol. 85, No. 1, pp. 43–49 (1995).
Angela Hague et al., "Apoptosis in Colorectal Tumour Cells: Induction by the Short Chain Fatty Acids Butyrate, Propionate and Acetate and by the Bile Salt Deoxycholate," *Int. J. Cancer*, vol. 60, pp. 400–406 (1995).
Antonius A. Miller et al., "Clinical Pharmacology of Sodium Butyrate in Patients with Acute Leukemia," *Eur. J. Cancer Clin. Oncol.*, vol. 23, No. 9, pp. 1283–1287 (1987).
Harold L. Newmark et al, "Butyrate as a Differentiating Agent: Pharmacokinetics, Analogues and Current Status," *Cancer Letters*, vol. 78, pp. 1–5 (1994).

Harold L. Newmark and Charles W. Young, "Butyrate and Phenylacetate as Differentiating Agents: Practical Problems and Opportunities," *J. Cell. Biochem.*, Supplement 22, pp. 247–253 (1995).
Abraham Novogrodsky et al., "Effect of Polar Organic Compounds on Leukemic Cells: Butyrate–Induced Partial Remission of Acute Myelogenous Leukemia in a Child," *Cancer*, vol. 51, No. 1, pp. 9–14 (1983).
Abraham Nudelman et al., "Novel Anticancer Prodrugs of Butyric Acid," *J. Med. Chem.*, vol. 35, pp. 694–704 (1992).
Michiro Otaka et al., "Antibody–Mediated Targeting of Differentiation Inducers to Tumor Cells: Inhibition of Colonic Cancer Cell Growth In Vitro and In Vivo, A Preliminary Note," *Biochem. Biophy. Res. Comm.*, vol. 158, No. 1, pp. 202–208 (1989).
Philippe Pouillart et al, "Butyric Monosaccharide Ester–Induced Cell Differentiation And Anti–Tumor Activity In Mice. Importance Of Their Prolonged Biological Effect For Clinical Applications In Cancer Therapy," *Int. J. Cancer*, vol. 49, pp. 89–95 (1991).
Philippe Pouillart et al., "Pharmacokinetic Studies of N–Butyric Acid Mono–and Polyesters Derived from Monosaccharides," *J. Pharm. Sci.*, vol. 81, No. 3, pp. 241–244 (1992).
K. N. Prasad, "Butyric Acid: A Small Fatty Acid with Diverse Biological Functions," *Life Sci.*, vol. 27, pp. 1351–1358 (1980).
O. C. Velazquez et al., "Butyrate and the Colonocyte: Implications for Neoplasia," *Dig. Dis. Sci.*, vol. 41, pp. 727–739 (1996).

*Primary Examiner*—Jerome D. Goldberg
*Attorney, Agent, or Firm*—Fish & Neave; James F. Haley, Jr.; Margaret A. Pierri

[57] ABSTRACT

The present invention relates to the use of butyrate esters of threitol, alone or in combination with other agents, in pharmaceutical compositions and methods for increasing fetal hemoglobin and gamma globin in a patient. These methods are particularly useful in treating β-hemoglobinopathies, such as sickle cell syndromes and β-thalassemia syndromes. Compositions comprising butyrate esters of threitol, alone or in combination antiproliferative and differentiating agents are also useful in methods for inducing cell differentiation in malignant cells. These methods are useful in treating cancer, particularly the tetrabutyrate ester.

15 Claims, No Drawings

METHODS AND COMPOSITIONS USING BUTYRATE ESTERS OF THREITOL

This is a division of application Ser. No. 08/550,453, filed Oct. 30, 1995, now U.S. Pat. No. 5,763,488, entitled METHODS AND COMPOSITIONS USING BUTYRATE ESTERS OF THREITOL.

TECHNICAL FIELD OF THE INVENTION

The present invention relates to the use of butyrate esters of threitol, alone or in combination with other agents, in pharmaceutical compositions and methods for increasing fetal hemoglobin and gamma globin in a patient. These methods are particularly useful in treating β-hemoglobinopathies, such as sickle cell syndromes and β-thalassemia syndromes. Compositions comprising butyrate esters of threitol, alone or in combination antiproliferative and differentiating agents are also useful in methods for inducing cell differentiation in malignant cells. These methods are useful in treating cancer, particularly the tetrabutyrate ester.

BACKGROUND OF THE INVENTION

β-hemoglobinopathies are a group of inherited disorders of β-globin biosynthesis. Although efforts have concentrated on a variety of therapeutic regimens, feasible clinical treatments for these debilitating diseases remain scarce.

Various therapies have been utilized in the treatment of β-hemoglobinopathies, each accompanied by drawbacks [G. P. Rogers et al., "Current and Future Strategies for the Managements of Hemoglobinopathies and Thalassemia", *Hematology* 1994, Education Program American Society of Hematology, pp. 9–20 (1994)]. Although hydroxyurea stimulates fetal hemoglobin production and reduces sickling crisis in sickle cell anemia patients, its use is potentially limited by myelotoxicity and the risk of carcinogenesis. Potential long term carcinogenicity is also a drawback of 5-azacytidine-based therapies. Red blood cell transfusions expose patients to the potential of a wide range of infectious viral agents, alloimmunization and iron overload. Bone marrow transplants are not a readily available option for a large number of patients. Erythropoietin-based therapies have not proved consistent among a range of patient populations. Such varying drawbacks contraindicate the long term use of such agents or therapies.

It is clear from multicenter studies involving numerous patients with sickle cell disease that increased blood levels of fetal hemoglobin are associated with lower events of sickle cell crisis and longer survival time [Platt et al., "Pain in Sickle Cell Disease, *New Eng. J. Med.*, 325, pp. 11–16 (1991); Platt et al., "Mortality ion Sickle Cell Disease", *New Eng. J. Med.*, 330, pp. 1639–44 (1994)]. Accordingly, in an effort to avoid the disadvantages of conventional therapies for β-hemoglobinopathies, therapies have centered around ways to increase fetal hemoglobin production. Recent clinical trials have focused on the use of butyrate analogs, including arginine butyrate and isobutyramide, to stimulate fetal hemoglobin production as a means of treatment [S. Perrine et al., "A Short Term Trial of Butyrate to Stimulate Fetal-Globin-Gene Expression in the β-globin Disorders", *N. Eng. J. Med.*, 328, pp. 81–86 (1993); S. P. Perrine et al., "Isobutyramide, an Orally Bioavailable Butyrate Analogue, Stimulates Fetal Globin Gene Expression in vitro and in vivo," *British J. Haematology*, 88, pp. 555–61 (1994); A. F. Collins et al., "Oral Sodium Phenylbutyrate Therapy in Homozygous β Thalassemia: A Clinical Trial", *Blood*, 85, pp. 43–49 (1995)]. Clinical trials have also employed sodium phenylbutyrate as a hemoglobin switching agent for β-thalassemia [Collins et al., supra].

Following the observation that butyric acid induces cell differentiation in vitro [A. Leder and P. Leder, "Butyric Acid, a Potent Inducer of Erythroid Differentiation in Cultured Erythroleukemic Cells", *Cell*, 5, pp. 319–22 (1975)], that compound was found to demonstrate promising effects in leukemia patients, by inducing cell differentiation [A. Novogrodsky et al., "Effect of Polar Organic Compounds on Leukemic Cells", *Cancer*, 51, pp. 9–14 (1983)]. Aside from their use in treating β-hemoglobinopathies, butyrate derivatives such as arginine butyrate, an arginine salt of butyric acid, have been shown to exert anti-tumor and anti-leukemia effects in mice [C. Chany and I. Cerutti, "Antitumor Effect Of Arginine Butyrate in Conjunction with *Corynebacterium Parvum* and Interferon", *Int. J. Cancer*, 30, pp. 489–93 (1982); M. Otaka et al., "Antibody-Mediated Targeting of Differentiation Inducers To Tumor Cells: Inhibition of Colonic Cancer Cell Growth in vitro and in vivo", *Biochem. Biophys. Res. Commun.*, 158, pp. 202–08 (1989)].

Although butyrate salts have the advantage of low toxicity as compared with conventional chemotherapeutic agents, their short half-lives in vivo have been viewed as a potential obstacle in clinical settings [A. Miller et al., "Clinical Pharmacology of Sodium Butyrate in Patients with Acute Leukemia", *Eur. J. Clin. Oncol.*, 23, pp. 1283–87 (1987); Novogrodsky et al., supra]. The rapid clearance of these agents results in an inability to deliver and maintain high plasma levels of butyrate and necessitates administration by intravenous infusion. Another potential obstacle to the use of butyrate salts is salt overload and its physiological sequelae.

In view of these observations, various prodrugs of butyric acid have been proposed for use in β-hemoglobinopathy and leukemia differentiation therapies. Such prodrugs include tributyrin and n-butyric acid mono- and polyesters derived from monosaccharides [Z. Chen and T. Breitman, "Tributyrin: A Prodrug of Butyric Acid for Potential Clinical Application in Differentiation Therapy", *Cancer Res.*, 54, pp. 3494–99 (1994); H. Newmark et al., "Butyrate as a Differentiating Agent: Pharmacokinetics, Analogues and Current Status", *Cancer Letts.*, 78, pp. 1–5 (1994); P. Pouillart et al., "Pharmacokinetic Studies of N-Butyric Acid Mono- and Polyesters Derived From Monosaccharides", *J. Pharm. Sci.*, 81, pp. 241–44 (1992)]. Such prodrugs have not proved useful as therapeutics, however, due to factors such as low bioavailability, lack of effective oral deliverability, short half life, low $C_{max}$ or high pharmacokinetic variability. Other prodrugs, such as AN-9 and AN-10, elicit metabolites that may produce formaldehyde in vivo, which may lead to toxic effects in patients.

To date, conventional methods and therapeutic agents have not proved to be safe and effective for all patients in the long term treatment of β-hemoglobinopathies. This is also the case for diseases characterized by neoplastic, tumorigenic or malignant cell growth, or malignant hematological disorders. Accordingly, the need exists for alternatives having advantages over, and avoiding the disadvantages of, such conventional methods and agents, while providing effective therapy for those target diseases.

DISCLOSURE OF THE INVENTION

The present invention solves these problems by providing methods and compositions utilizing butyrate esters of threitol for increasing fetal hemoglobin and gamma globin production in a patient. These butyrate esters demonstrate good bioavailability, effective oral deliverability, good half-life, good $C_{max}$ and surprisingly low pharmacokinetic variability between individual patients. This last factor increases their utility as agents to deliver therapeutically effective amounts of systemic butyrate.

The compositions and methods of the invention are especially useful for treating or reducing the advancement, severity, symptoms or effects of β-hemoglobinopathies, including sickle cell syndromes and β-thalassemia syndromes. In addition, the methods and compositions according to the present invention are useful for stimulating cell differentiation in malignant cells. Such compositions and methods are useful for treating cancer.

Accordingly, the methods and compositions of this invention are not beset by the variety of side effects which typically characterize conventional therapy regimens.

DETAILED DESCRIPTION OF THE INVENTION

In order that the invention herein described may be more fully understood, the following detailed description is set forth.

According to one embodiment, this invention provides pharmaceutical compositions comprising a butyrate ester of threitol represented by the formula:

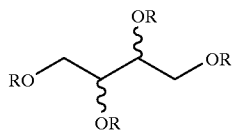

wherein R is

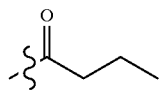

or hydrogen, provided that at least one R is

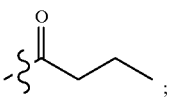

and
the stereochemistry at the achiral carbons is independently selected from R or S and a pharmaceutically acceptable carrier or adjuvant. Preferably each R is

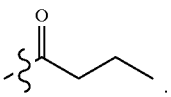

More preferably, the pharmaceutical compositions of this invention comprise an approximately equimolar mixture of (R) and (S) configurations presented by the following Fischer projections:

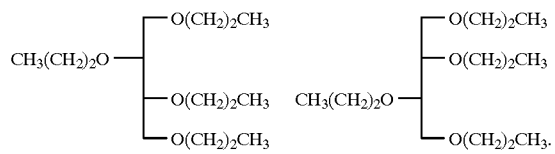

The tetrabutyrate esters of threitol and the partially esterified analogs of threitol useful in the methods and compositions of the present invention may be synthesized by conventional techniques. Advantageously, these compounds are conveniently synthesized from commercially available starting materials. For example, they may be prepared from the D-, L- or D,L-forms of threitol using an appropriate activated reagent, such as an activated butyric acid derivative, in conventional esterification techniques. For instance, reaction with an activated carboxylate, such as an acyl halide (e.g., acid fluorides, acid chlorides, and acid bromides), an acyl cyamide of acyl imidazolide, an activated ester such as nitrophenyl ester or 1-hydroxysuccinimide (HOSu) ester, an anhydride such as the symmetrical anhydride or isobutyl mixed carbonic anhydride, or mixed carbonic-phosphoric or carbonic-phosphonic anhydrides with an appropriate alcohol, will yield the corresponding ester.

Other methods of forming esters from alcohols and carboxylic acids or their derivatives are also well known to those of skill in the art. These include removal of water by Dean-Stark distillation, Fischer esterification and transesterification. Various catalysts and additives, including protic and/or Lewis acids, bases or zeolites may be used to increase the ease or efficiency of these reactions. Enzymatic methods to form esters are also well known in the art.

Specific modifications of these methods, as well as other means of forming esters are known by those of skill in the art. It will be readily recognized that in order to facilitate specific reactions, the protection of one or more potentially reactive groups followed by subsequent removal of that group may be required. Such modifications are within the skill of the art.

In any synthesis method, the desired compound may be isolated by any technique, including, for example, distillation, chromatographic techniques, such as normal phase, reverse phase, ion-exchange, affinity, or gel permeation, as well as extraction, crystallization, or other means. The relative ease of synthesis of the compounds of this invention represents an advantage in their large scale production.

It should also be understood that the butyrate esters of threitol used in the compositions of this invention may be modified by appending appropriate functionalities to enhance selective biological properties. Such modifications are well recognized in the art and include sustenance of plasma and/or whole blood butyrate concentration, increased oral availability, altered metabolism and altered rate of excretion of butyric acid or butyric acid prodrugs.

The pharmaceutical compositions of this invention are characterized by the presence of a butyrate ester of threitol in an amount effective to increase the production of fetal hemoglobin or stimulate cell differentiation in a patient and a pharmaceutically acceptable carrier or adjuvant. More specifically, these compositions are designed to treat a patient suffering from a β-hemoglobinopathy or a malignant disease. The term "malignant disease", as used herein denotes a condition characterized by neoplastic, tumorigenic or malignant cell growth, or a hematological disorder.

An amount effective to increase the production of fetal hemoglobin or stimulate cell differentiation in a patient will depend, of course, on the particular disease to be treated, the severity of the disease, the physical condition of the patient and the judgment of the treating physician. Preferably, the prodrug of Formula I will be present in an amount capable of producing a plasma butyric acid concentration of between about 0.03 mM and 3.0 mM within 8 hours of administration. More preferably, the prodrug of Formula I is present in an amount that produces a plasma butyric acid concentration of between about 0.1 mM and 1.0 mM within 6 hours of administration. Most preferably, the prodrug in the composition is present in an amount that produces a plasma butyric acid concentration of between about 0.1 mM and 1.0 mM within 2 hours of administration and the concentration remains at those levels for at least 2 hours. Dosages of between 25 mg/kg and 3000 mg/kg body weight of butyrate ester of threitol administered one or more time per day will produce the desired serum butyrate concentration. Preferably, the patient will be administered the prodrug between 1 and 4 times per day.

In a preferred embodiment, these compositions additionally comprise a conventional agent used in the treatment of β-hemoglobinopathies. The conventional agent may be present in the same amount or less than that normally required to treat β-hemoglobinopathies in a monotherapy. The normal dosages of these conventional agents are well known in the art. Such agents include hydroxyurea, clotrimazole, isobutyramide, erythropoietin and salts of short-chain fatty acids, such as phenylacetic acid, phenylbutyric acid and valproic acid.

According to an alternate preferred embodiment, the compositions comprise a butyrate ester of threitol and a conventional agent used in the treatment of diseases characterized by neoplastic, tumorigenic or malignant cell growth, or a hematological disorder in a patient. This additional agent may be present in an amount equal to or less than that normally required to treat such diseases in a monotherapy. The normal dosages of these conventional agents are well known in the art. Such agents include, erythropoietin, or cancer chemotherapeutic agents, such as hydroxyurea or 5-azacytidine.

The carriers and adjuvants useful in the pharmaceutical compositions of this invention include, for example, ion exchangers, alumina, aluminum stearate, lecithin, serum proteins, such as human serum albumin, buffer substances, such as phosphates, glycine, sorbic acid, potassium sorbate, partial glyceride mixtures of saturated vegetable fatty acids, water, salts or electrolytes such as protamine sulfate, disodium hydrogen phosphate, sodium chloride, zinc salts, colloidal silica, magnesium, trisilicate, polyvinyl pyrrolidone, cellulose-based substances and polyethylene glycol. Adjuvants for topical or gel base forms may be selected from the group consisting of sodium carboxymethylcellulose, polyacrylates, polyoxyethylene-polyoxypropylene-block polymers, polyethylene glycol and wood wax alcohols.

The compositions of the present invention may be in a variety of conventional depot forms. These include, for example, solid, semi-solid and liquid dosage forms, such as tablets, pills, powders, liquid solutions or suspensions, oil dilutions, liposomes, capsules, suppositories, injectable and infusible solutions. The preferred form depends upon the intended mode of administration and therapeutic application.

For example, oral administration may be by any orally acceptable dosage form including, but not limited to, capsules, tablets, and aqueous or non-aqueous suspensions and solutions. In the case of tablets for oral use, carriers which are commonly used include lactose and corn starch. Lubricating agents, such as magnesium stearate, are also typically added. For oral administration in a hard gelatin capsule form, useful diluents include lactose and dried corn starch. Soft gelatin capsules incorporating oils and/or polyethylene glycols as excipients may also be used. Fluid unit dosage forms for oral administration include syrups and suspensions. For example, the butyrate ester of threitol may be dissolved in an aqueous vehicle together with sugar, sweetening or flavoring agents and preservatives to form a syrup. Suspensions may be prepared with an aqueous vehicle and a dispersing agent, such as acacia, tragacanth or methylcellulose.

Preferably, the pharmaceutical compositions of this invention are formulated for oral administration. Even more preferred are oral emulsions comprising between about 5 to 40% (w/w) of the prodrug of formula I and an ionic or non-ionic surfactant with the resulting composition having an HLB value of between 0–40. Preferred surfactants include Tween-20, Tween-80, Spam-20, Spam-40 and poloxamers, such as S-108.

The butyrate esters of threitol which characterize the compositions of this invention are characterized by several advantages. They are metabolized to yield therapeutic butyric acid plasma concentrations over a sustained period of time, resulting in therapeutically effective exposure to butyric acid. Additionally, they are orally bioavailable, unlike sodium butyrate—which is rapidly cleared before therapeutic plasma concentration levels can be reached. They are also non-toxic, thus avoiding, for example, sodium overload and irritation which may be associated with injections of hyperosmolalic solutions.

The most surprising and unexpected feature of the butyrate esters of threitol that characterize the pharmaceutical compositions of this invention is that they exhibit significantly lower pharmacokinetic variability over conventional prodrugs of butyric acid. Pharmacokinetic variability is the measure of differences in the serum butyrate concentrations between different patients administered the same amount of butyrate esters of threitol. Pharmacokinetic variability is quantified by dividing the standard deviation for a given parameter, such as $C_{max}$ or AUC, by the mean value of that parameter, in a series of patients given dose the same dosage of butyrate ester of threitol.

In particular, the tetrabutyrate ester of mesothreitol is characterized by a pharmacokinetic variability of 35–40%, as compared with conventional prodrugs of butyric acid, such as tributyrin, which has a pharmacokinetic variability of 70%. This reduced variability means that the compositions of this invention provide sustained release and produce more consistent plasma concentrations of butyric acid among individual patients. This, in turn, minimizes the potential for cellular toxicity, which, based on our own in vitro cell culture studies, has been observed at butyric acid concentrations above 3.0 mM under certain in vitro conditions.

According to another embodiment, the invention provides methods for treating a β-hemoglobinopathy in a patient. This method comprises the step of treating the patient with any of the compositions described above. The term "treating", as used herein includes reducing the severity, symptoms or effects of the β-hemoglobinopathy.

Preferably, the method provides a serum butyric acid concentration of between about 0.03 mM and 3.0 mM within about 8 hours of administration. More preferably, this produces a plasma butyric acid concentration of between about 0.1 mM and 1.0 mM within about 6 hours of administration. Most preferably, the prodrug in the composition is present in an amount that produces a plasma butyric acid concentration of between about 0.1 mM and 1.0 mM within 2 hours of administration and the concentration remains within that range for at least 2 hours. These plasma levels are achieved by administering a butyrate ester of threitol to the patient at a dose of between about 25–3000 mg/kg body weight one or more times per day. Preferably, the patient will be administered the prodrug between 1 and 4 times per day.

The β-hemoglobinopathies which may be treated by this method include sickle cell syndromes, such as sickle cell anemia, hemoglobin SC disease, hemoglobin SS disease and sickle β-thalassemia; β-thalassemia syndromes, such as β-thalassemia; other genetic mutations of the β-globin gene locus that lead to unstable hemoglobins, such as congenital Heinz body anemia, β-globin mutants with abnormal oxygen affinity and structural mutants of β-globin that result in thalassemic phenotype. These diseases are described in *The Molecular Basis of Blood Disease*, vol. II, G. Stamatoyannopoulos et at., eds., pp. 157–244 (1994).

According to a preferred embodiment, the above-described method comprises the additional step of treating the patient with an agent that is normally used to treat such β-hemoglobinopathies. That agent may be administered prior to, sequentially with or after treatment with the butyrate prodrug-containing composition. Of course, if the composition used to treat the disease is one that already contains such conventional agent, this additional step can be omitted.

The amount of conventional agent administered in these methods is preferably less than that normally required to treat such diseases in a monotherapy. The normal dosages of these conventional agents are well known in the art. Such agents include hydroxyurea, clotrimazole, isobutyramide, erythropoietin and salts of short-chain fatty acids, such as phenylacetic acid, phenylbutyric acid and valproic acid.

According to another embodiment, the invention provides method for treating diseases characterized by neoplastic, tumorigenic or malignant cell growth, as well as malignant hematological disorders. Treatment includes prevention of the progression of the disease or its recurrence. Such diseases include carcinomas, myelomas, melanomas, lymphomas and leukemias. Preferably, the method provides the same serum butyric acid concentrations indicated above as being desirable for treating β-hemoglobinopathies.

According to a preferred embodiment, the above-described method comprises the additional step of treating the patient with an agent that is normally used to treat such malignancies. That agent may be administered prior to, sequentially with or after treatment with the butyrate prodrug-containing composition. Of course, if the composition used to treat the disease is one that already contains such conventional agent, this additional step can be omitted.

The amount of conventional agent administered in these methods is preferably less than that normally required to treat such diseases in a monotherapy. In those instances, the occurrence of any side effects associated with that agent may be reduced or avoided. The normal dosages of these conventional agents are well known in the art. Such agents include, erythropoietin, or cancer chemotherapeutic agents, such as hydroxyurea or 5-azacytidine.

Combination therapies with conventional agents according to this invention (whether part of a single composition or administered separate from the prodrugs of this invention) may also exert an additive or synergistic effect, particularly when each component acts to treat or prevent the target disease via a different mechanism.

In order that the invention described herein may be more fully understood, the following examples are set forth. It should be understood that these examples are set forth for illustrative purposes only and are not to be construed as limiting this invention in any manner.

EXAMPLE 1

Synthesis of d-, l- and d,l-Threitol Tetrabutyrate Esters

We synthesized d-threitol tetrabutyrate ester as follows. We added 17 ml of $Et_3N$ to 3.0 g of D-threitol dissolved in $CH_2Cl_2$ and cooled the mixture to 0° C. We then added 11 ml of $CH_3(CH_2)_2COCl$ in 5 ml $CH_2Cl_2$ over 30 minutes. The reaction mixture was stirred at room temperature overnight. We then diluted the reaction with ether and filtered the resulting material. The precipitate was washed once over a filter with ether. The filtrates were combined, washed twice with water, once with saturated NaCl and dried over $MgSO_4$, filtered and concentrated.

The resulting yellow oil was run on an MPLC column in 90:10 (hexane:EtoAc). The yield of purified product was 8.35g of a light yellow oil.

We synthesized d-, l-threitol tetrabutyrate ester using the same methodology replacing D-threitol with D,L-threitol using the same ratio of equivalents (1:5:4.5; threitol:$Et_3N$:$CH_3(CH_2)_2COCl$).

The structure of the purified compounds was confirmed by NMR.

EXAMPLE 2

Oral Availability of Butyrate Esters of Threitol in Rats

We evaluated oral bioavailability and sustenance of plasma concentrations of butyric acid in rats receiving tetrabutyrate esters of threitol and tributyrin by oral gavage.

This assay was carried out according to the protocol described in Daniel et al., *Clinca Chimica Acta.*, 181, pp. 255–64 (1989); Planchon et al., *J. Pharm. Sci.*, 82, pp. 1046–48 (1993); Pouillart et al., *J. Pharm Sci.*, 81, pp. 241–44 (1992). Each compound was tested in five to six rats (Sprague Dawley; Harlan Labs, Inc.) weighing approximately 300 grams each. The relevant pharmacokinetic parameters for these agents are listed in the table below. In that table, data are expressed as mean ± standard deviation (range) and were compared using the unpaired Student's t-test.

TABLE 1.

Pharmokinetics of butyrate esters of threitol in rats.

| Compound | Dose (gm/kg) | Number of animals | AUC (mM · hr) | $C_{max}$ (mM) | Plasma $t_{1/2}$ (mins) |
|---|---|---|---|---|---|
| tributyrin | 3.0 | 6 | 1.59 ± 0.93 | 0.51 ± 0.46 | 157.2 ± 70.2 |
| l-threitol tetrabutyrate ester | 2.4 | 5 | 1.20 ± 0.40 | 0.58 ± 0.13 | 66.0 ± 12.0 |
| d-threitol tetrabutyrate ester | 2.8 | 6 | 0.90 ± 0.26 | 0.47 ± 0.14 | 58.8 ± 19.8 |
| dl-threitol tetrabutyrate ester | 3.0 | 5 | 1.25 ± 0.22 | 0.39 ± 0.12 | 106.2 ± 22.2* |

* Significantly different from l-threitol tetrabutyrate ester and d-threitol tetrabutyrate ester (p < 0.01).

As shown above, the tetrabutyrate esters of threitol were found to release butyric acid in vivo with lower variability than tributyrin. Oral administration of each of those prodrugs of butyric acid also increased the "apparent" plasma half-life of butyric acid to significantly longer than the 6 minutes observed in leukemia patients after continuous infusions of sodium butyrate [Miller et al., supra]. The area under the plasma concentration-time curve and the observed $C_{max}$ values for butyric acid were not significantly different for any of the tetrabutyrate esters or tributyrin (following dose-normalization). Advantageously and unexpectedly, the butyrate ester of D,L-threitol was found to have an "apparent" butyric acid plasma half-life which was significantly longer than that observed for the tetrabutyrate ester of either D-threitol or L-threitol.

A closer examination of the data showed that the release of butyric acid from tributyrin was more variable when compared to that obtained following oral administration of the tetrabutyrate ester of D,L-threitol. The pharmacokinetic variability with tributyrin oral administration is demonstrated by the wide range of $C_{max}$ (0.295 to 1.46 mM); AUC (0.72 to 3.23 mM.hr); and plasma half-life (67.2 to 259.8 minutes). On the other hand, the ranges for $C_{max}$, AUC and plasma half-life for orally administered tetrabutyrate ester of D,L-threitol were 0.26 to 0.545 mM, 0.95 to 1.53 mM.hr and 79.2 to 126.9 minutes, respectively. Thus, both tributyrin and the tetrabutyrate ester of D,L-threitol are orally bio-available to provide therapeutic plasma levels of butyric acid. However, a clear advantage of that tetrabutyrate ester is its reduced pharmacokinetic variability—signifying a consistent pharmacokinetic profile which, in turn, enables more reliable clinical treatment regimens than those based on tributyrin.

While we have hereinbefore described a number of embodiments of this invention, it is apparent that our basic constructions can be altered to provide other embodiments which utilize the processes and compositions of this invention. Therefore, it will be appreciated that the scope of this invention is to be defined by the claims appended hereto rather than by the specific embodiments which have been presented hereinbefore by way of example.

We claim:

1. A method of inducing differentiation in a malignant cell comprising the step of contacting said cell with a pharmaceutical composition comprising:

a. an amount of a butyrate ester of threitol effective to induce differentiation in malignant cells sensitive to said butyrate ester in a patient; and b. a pharmaceutically acceptable adjuvant or carrier;

said butyrate ester of threitol having the formula:

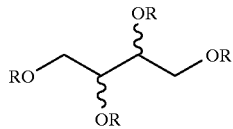

wherein each R is independently selected from

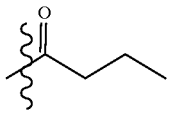

2. The method according to claim 1, wherein said pharmaceutical composition comprises a mixture of

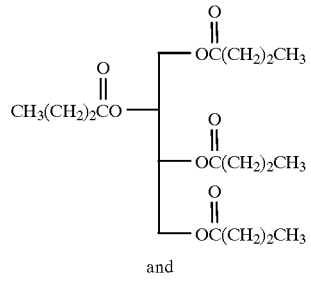

and

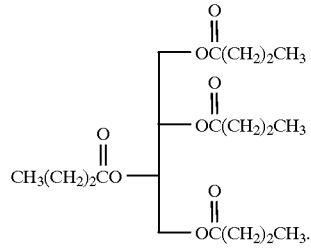

3. The method according to any one of claims 1, or 2, wherein said pharmaceutical composition is an emulsion formulated for oral administration.

4. The method according to any one of claims 1, or 3, wherein said method is used to treat cancer in a patient.

5. The method according to claim 4, wherein said method produces a serum butyric acid concentration of between about 0.1 mM and 1.0 mM within 2 hours of administration and the serum butyric acid concentration remains between about 0.1 mM and 1.0 mM for at least 2 hours.

6. The method according to claim 4, wherein said cancer is selected from the group consisting of carcinomas, myelomas, melanomas, lymphomas and leukemias.

7. The method according to claim 4, wherein said pharmaceutical composition is administered to said patient orally.

8. The method according to claim 4, comprising the additional step of administering to said patient an agent used in the treatment of diseases characterized by neoplastic, tumorigenic or malignant cell growth in an amount equal to or less than an amount of said agent used in a monotherapy.

9. The method according to claim 8, wherein said agent is erythropoietin.

10. The method according to claim 8, wherein said agent is hydroxyurea or 5-azacytidine.

11. A pharmaceutical composition comprising:
   a. an amount of a butyrate ester of threitol effective to induce differentiation in malignant cells sensitive to said butyrate ester in a patient;
   b. an amount of an agent used in the treatment of diseases characterized by neoplastic, tumorigenic or malignant cell growth equal to or less than an amount of said agent used in a monotherapy; and
   c. a pharmaceutically acceptable adjuvant or carrier; said butyrate ester of threitol having the formula:

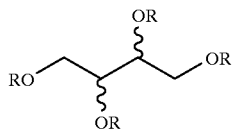

wherein each R is independently selected from

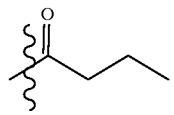

12. The pharmaceutical composition according to claim 11, wherein said agent is erythropoietin.

13. The pharmaceutical composition according to claim 11, wherein said agent is hydroxyurea or 5-azacytidine.

14. The pharmaceutical composition according to claim 7, comprising a mixture of

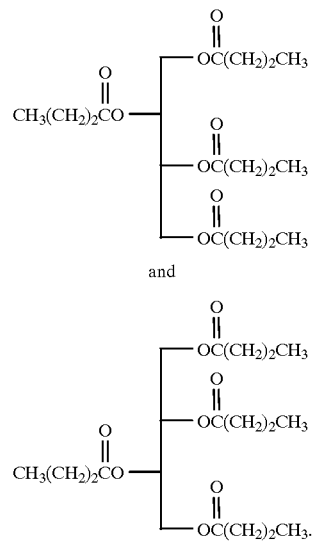

15. The pharmaceutical composition according to any one of claims 14, 11, 12 or 13, wherein said composition is an emulsion formulated for oral administration.

* * * * *